(12) United States Patent
Steiner et al.

(10) Patent No.: US 8,461,219 B2
(45) Date of Patent: Jun. 11, 2013

(54) PROCESS FOR THE SELECTIVE PREPARATION OF LIGHT OLEFINS

(75) Inventors: Jochen Steiner, Bensheim (DE); Kerem Bay, Ludwigshafen (DE); Ekkehard Schwab, Neustadt (DE); Alexander Weck, Freinsheim (DE)

(73) Assignee: BASF SE, Ludwigshafen (DE)

( * ) Notice: Subject to any disclaimer, the term of this patent is extended or adjusted under 35 U.S.C. 154(b) by 222 days.

(21) Appl. No.: 12/950,646

(22) Filed: Nov. 19, 2010

(65) Prior Publication Data

US 2011/0118365 A1    May 19, 2011

(30) Foreign Application Priority Data

Nov. 19, 2009    (EP) .................................. 09176550

(51) Int. Cl.
*C07C 27/00*    (2006.01)
(52) U.S. Cl.
USPC ........... 518/705; 518/703; 518/704; 518/715; 518/717
(58) Field of Classification Search
USPC .................. 518/700, 703, 704, 705, 715, 717
See application file for complete search history.

(56) References Cited

U.S. PATENT DOCUMENTS 4,261,865 A  *  4/1981 Hargis ........................... 502/330
4,510,267 A  *  4/1985 Pierantozzi ................... 518/715

FOREIGN PATENT DOCUMENTS

| WO | WO-2009/013174 A2 | 1/2009 |
| WO | WO-2009/051353 A2 | 4/2009 |
| WO | WO2009/071463 | 11/2009 |
| WO | WO 2010/028995 | 3/2010 |
| WO | WO2010/054976 | 5/2010 |

OTHER PUBLICATIONS

U.S. Appl. No. 13/063,321, filed Mar. 10, 2011, Steiner et al.
U.S. Appl. No. 12/939,281, filed Nov. 4, 2010, Steiner et al.
U.S. Appl. No. 12/940,772, filed Nov. 5, 2010, Steiner et al.
U.S. Appl. No. 12/939,903, filed Nov. 4, 2010, Steiner et al.
Weissermehl et al., Industrial Organic Chemistry, WhileyVCH, Weinheim, 2004, pp. 15-24.
C. D. Frohning et al., in "Chemierohstoffe aus Kohle", 1977, pp. 219-299.
B. H. Davis, Tropcs and Catalysis, 2005, 32 (3-4) pp. 143-168.

* cited by examiner

*Primary Examiner* — Jafar Parsa
(74) *Attorney, Agent, or Firm* — Novak Druce Connolly Bove + Quigg LLP

(57) ABSTRACT

Process for preparing olefins, which comprises the following steps:
a) preparation of a synthesis gas comprising carbon monoxide and hydrogen,
b) introduction of carbon dioxide recirculated from step d) into the synthesis gas during or after the preparation of synthesis gas as per step a),
c) conversion of the synthesis gas having a hydrogen to carbon monoxide ratio of $\leq 1.2:1$ which is obtained in step b) into olefins in the presence of a Fischer-Tropsch catalyst,
d) removal of the carbon dioxide comprised in the reaction product from step c),
where the ratio of hydrogen to carbon monoxide in step c) is set via step b).

13 Claims, 4 Drawing Sheets

PROCESS FOR THE SELECTIVE PREPARATION OF LIGHT OLEFINS

CROSS-REFERENCE TO RELATED APPLICATIONS

This application claims benefit of European patent application no. 09176550.3 filed Nov. 19, 2009, the contents of which are incorporated herein by reference in its entirety.

FIELD OF THE INVENTION

The invention relates to a process for the selective preparation of olefins by means of the Fischer-Tropsch synthesis, in particular the selective preparation of $C_2$-$C_8$-olefins. Furthermore, the process is also low in emissions because the carbon dioxide formed, inter alia, as by-product in the Fischer-Tropsch synthesis is recirculated to the process.

BACKGROUND OF THE INVENTION

Linear or branched alkenes having from 2 to 8, preferably from 2 to 6 and in particular from 2 to 4, carbon atoms are also referred to as lower or light olefins. It is known, for example from WO 2009/013174, that light olefins can be prepared from carbon monoxide (CO) and hydrogen ($H_2$) over metal catalysts, for example iron or cobalt catalysts.

The term Fischer-Tropsch synthesis generally refers to the reaction of carbon monoxide with hydrogen in the presence of a heterogeneous catalyst. A mixture comprising essentially carbon monoxide and hydrogen, preferably prepared from natural gas by reaction with water (or oxygen), is also referred to as synthesis gas.

$$CH_4 + H_2O \rightleftharpoons CO + 3H_2 \quad (1)$$

Hydrocarbons, in particular alkanes and olefins, are prepared by means of the Fischer-Tropsch synthesis by reaction of the components of synthesis gas over a suitable heterogeneous catalyst, with the product distribution depending greatly on the reaction parameters set. The chemical reaction equation for the synthesis of olefins is shown below.

$$2nH_2 + nCO \rightarrow C_nH_{2n} + nH_2O \quad (2)$$

In general, additional hydrogen is formed from water and carbon monoxide in the presence of an iron-comprising catalyst, as a result of which an excess of hydrogen over carbon monoxide is frequently present during the process in a Fischer-Tropsch synthesis. Carbon monoxide and hydrogen are in equilibrium with one another, with the greenhouse gas carbon dioxide ($CO_2$) also being formed on the side of hydrogen (see equation (3)). Furthermore, additional carbon dioxide is formed as by-product in the Fischer-Tropsch synthesis.

$$CO + H_2O \rightleftharpoons H_2 + CO_2 \quad (3)$$

WO 2009/013174 A2 describes a process for preparing olefins by reacting carbon monoxide with hydrogen in the presence of an iron-comprising heterogeneous catalyst which comprises essentially a carbonyl iron powder catalyst having spherical primary particles.

WO-A 2009/051353 describes a process for the direct synthesis of light hydrocarbons from natural gas. In the presence of a nickel-aluminum catalyst, synthesis gas having a molar ratio of carbon monoxide to hydrogen of 1:1.5-2.5 is firstly produced from natural gas in a steam reforming process. In the subsequent Fischer-Tropsch process, light saturated hydrocarbons ($C_2$-$C_4$) and, as by-products, methane, carbon dioxide and $C_2$-$C_4$-olefins are formed from carbon monoxide and hydrogen in the presence of an iron-copper-potassium zeolite catalyst. The by-products carbon dioxide and methane are subsequently recirculated to the process in the steam reforming step.

A problem in the Fischer-Tropsch synthesis (for the preparation of olefins) is the undesirable formation (emission) of carbon dioxide which acts as greenhouse gas and has a damaging effect on the environment.

SUMMARY OF THE INVENTION

It is an object of the present invention to provide a process by means of which the low-emission and/or selective preparation of olefins, preferably light olefins, via a Fischer-Tropsch synthesis process is made possible.

According to the invention, the object is achieved by a process for preparing olefins, which comprises the following steps:
a) preparation of a synthesis gas comprising carbon monoxide and hydrogen,
b) introduction of carbon dioxide recirculated from step d) into the synthesis gas during or after the preparation of synthesis gas as per step a),
c) conversion of the synthesis gas having a hydrogen to carbon monoxide ratio of $\leq 1.2:1$ which is obtained in step b) into olefins in the presence of a Fischer-Tropsch catalyst,
d) removal of the carbon dioxide comprised in the reaction product from step c), where the ratio of hydrogen to carbon monoxide in step c) is set via step b).

DETAILED DESCRIPTION OF THE PREFERRED EMBODIMENTS

Figure 1:
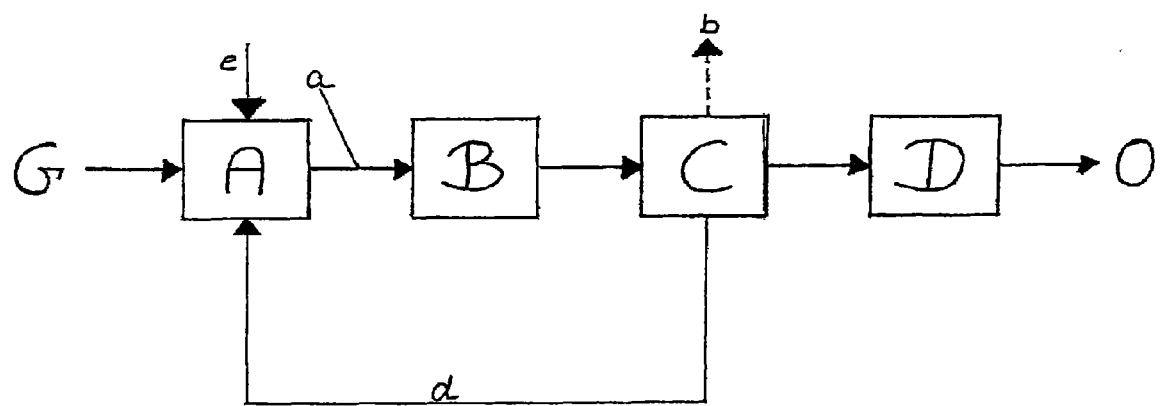
FIG. 1 depicts a dry reforming process.

In the process of the invention, preference is given to only the carbon dioxide separated off in step d) being recirculated and used in step b). The recirculated stream does not comprise any methane or only traces of methane.

The synthesis gas prepared in step a) can be prepared by generally known methods (as described, for example, in Weissermehl et al., Industrial Organic Chemistry, Wiley-VCH, Weinheim, 2003, pages 15 to 24).

The preparation of synthesis gas in step a) can be carried out using all processes known for this purpose. In one embodiment of the invention, a process selected from the group consisting of steam reforming, autothermal reforming, noncatalytic partial oxidation, catalytic partial oxidation, heat exchange reforming, compact reforming and dry reforming is used for the preparation of synthesis gas in step a).

The preparation of synthesis gas in step a) is preferably carried out by means of a steam reforming or dry reforming process.

In a preferred embodiment of the invention, the synthesis gas is prepared from methane and/or natural gas.

The synthesis gas is preferably prepared from a mixture comprising hydrocarbons having a ratio of hydrogen to carbon of 0.5 to 4:1 in step a).

In another embodiment of the invention said ratio is 1.2 to 5:1.

Suitable transition metal catalysts can be used for the preparation of synthesis gas in step a). However, these are frequently also used in combination with main group metals. Examples of metals which are employed in the preparation of synthesis gas are nickel and aluminum.

As Fischer-Tropsch catalysts, it is possible to use all catalysts which are known to those skilled in the art and are customary for Fischer-Tropsch syntheses. A Fischer-Tropsch catalyst which is an iron- or cobalt-comprising heterogeneous catalyst can preferably be used in step c).

A Fischer-Tropsch catalyst which is a carbonyl iron powder catalyst having spherical primary particles is particularly preferred in step c). Such catalysts are described in WO 2009/013174.

The process of the invention can be carried out in the presence of water or, if appropriate, other solvents. Suitable solvents are known to those skilled in the art.

The process of the invention can be carried out in all reactors which are known to those skilled in the art and are suitable for Fischer-Tropsch syntheses and have facilities for gas recirculation. In a further embodiment of the invention, fluidized-bed reactors, fixed-bed reactors and suspension reactors, preferably with a gas recirculation function, are used as reactors for carrying out the process of the invention.

The use of such reactors for the Fischer-Tropsch synthesis is described, for example, in C. D. Frohning et al. in "Chemierohstoffe aus Kohle", 1977, pages 219 to 299, or B. H. Davis, Tropics and Catalysis, 2005, 32 (3 to 4), pages 143 to 168.

In a particular embodiment of the invention, the hydrogen to carbon monoxide ratio in step c) is from 1.2:1 to 1:1.2.

In a further embodiment of the invention, the hydrogen to carbon monoxide ratio in step c) is from 1.1:1 to 1:1.1.

Particular preference is given to the hydrogen to carbon monoxide ratio in step c) being 1:1.1.

In another embodiment of the invention, the hydrogen to carbon monoxide ratio in step c) is 1:1.

In the process of the invention, the process temperature in step c) can be from 100° C. to 500° C.

In a further embodiment of the invention, step c) is carried out under superatmospheric pressure. The pressure can be in the range from 5 to 50 bar. Particular preference is given to the pressure in step c) being from 20 to 40 bar.

The process of the invention gives a product mixture comprising olefins, preferably light olefins ($C_2$-$C_8$-olefins), more preferably $C_2$-$C_6$-olefins, particularly preferably $C_2$-$C_4$-olefins, and also small amounts of aliphatic, saturated hydrocarbons having at least 2 carbon atoms. In the process of the invention, the yield of olefins is up to 47% by weight based on the total carbon yield.

The term "$C_2$-$C_8$-olefins" means that the respective olefins have at least 2 but not more than 8 carbon atoms. They can be linear or branched, and are preferably linear. Suitable $C_2$-$C_8$-olefins thus comprise ethene, propene, butene, pentene, hexene, heptene and octene.

The olefins obtained are, for example, used in processes for preparing polyolefins, epoxides, oxo products, acrylonitriles, acrolein, styrene.

The invention is described in more detail below with the aid of the figures.

FIG. 1 describes the invention in the embodiment via the dry reforming process

The natural gas (G) comprising essentially methane is fed into the natural gas reformer (A) for preparing the synthesis gas, with energy (e) being additionally introduced. A synthesis gas having a ratio of hydrogen to carbon monoxide of preferably 1:1 (a) is set by separating off carbon dioxide (d) during the reaction process and recirculating it to the natural gas reformer (A). This synthesis gas is then introduced into the Fischer-Tropsch reactor (B) and subjected to the Fischer-Tropsch synthesis process. The $CO_2$ which has, inter alia, been formed by the Fischer-Tropsch synthesis process is subsequently separated off in a carbon dioxide removal step (C), $CO_2$ which has been separated off (d) is recirculated to the natural gas reformer (A). In addition, small amounts of $CO_2$ (b) are discharged from the reaction process. The $CO_2$-depleted synthesis product is subjected to an olefin work-up (D) from which the olefins (O), preferably light olefins having $C_2$-$C_8$ chains, can then be obtained.

Figure 2:
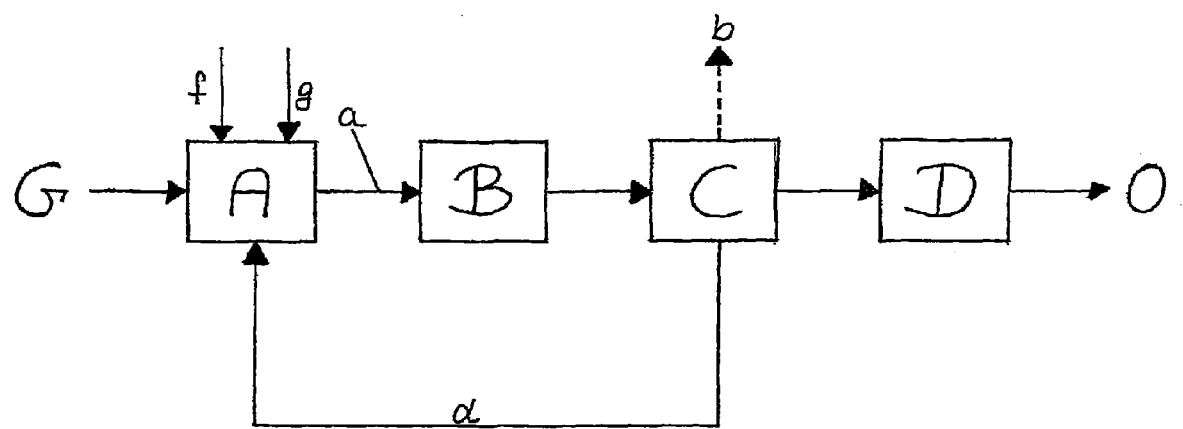
FIG. 2 depicts a steam reforming process.

FIG. 2 describes the invention in the embodiment via the steam reforming process The natural gas (G) comprising essentially methane is fed into the natural gas reformer (A), with oxygen (f) and/or water (g) being additionally fed in. A synthesis gas having a ratio of hydrogen to carbon monoxide of preferably 1:1 is set by separating off carbon dioxide (d) during the reaction process and recirculating it to the natural gas reformer (A). This synthesis gas is then introduced into the Fischer-Tropsch reactor (B) and subjected to the Fischer-Tropsch synthesis process. The $CO_2$ which has, inter alia, been formed by the Fischer-Tropsch synthesis process is subsequently separated off in a carbon dioxide removal step (C), and the $CO_2$ which has been separated off (d) is recirculated to the natural gas reformer (A). In addition, small amounts of $CO_2$ (b) are discharged from the reaction process. The $CO_2$-depleted synthesis product is subjected to an olefin work-up (D) from which the olefins (O), preferably light olefins having $C_2$-$C_8$ chains, can then be obtained.

Figure 3:
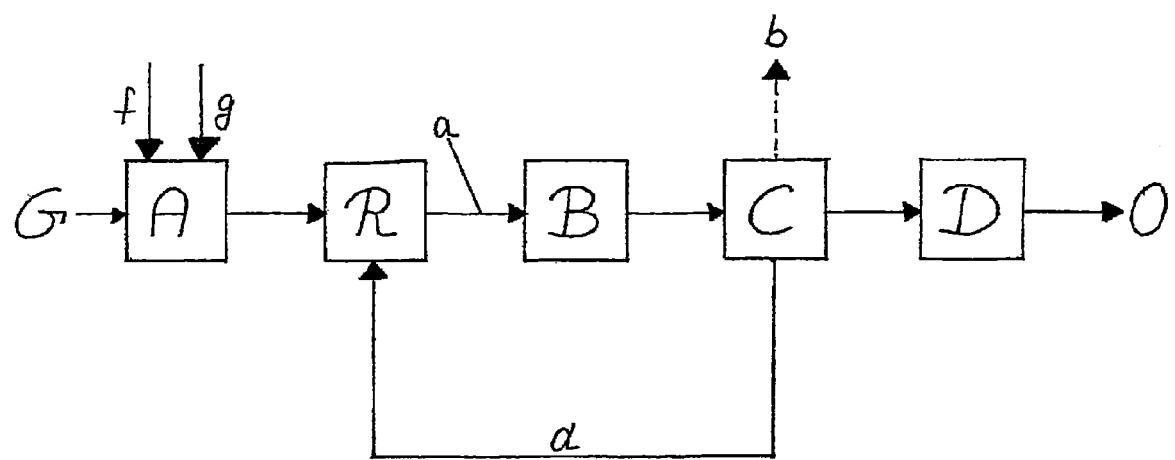
FIG. 3 depicts an intermediate reverse shift reactor.

FIG. 3 describes the invention in the embodiment with an intermediate reverse shift reactor The natural gas (G), which comprises mainly methane, is fed into the natural gas reformer (A). Oxygen (f) and/or water (g) are fed into the natural gas reformer (A). From this natural gas reformer (A), the synthesis gas is fed into a reverse shift reactor (R). The carbon dioxide (d) formed during the process is fed into this reverse shift reactor (R). A synthesis gas having a ratio of hydrogen to carbon monoxide of preferably 1:1 (a) is formed. This synthesis gas is fed into the Fischer-Tropsch reactor (B). The $CO_2$ which has, inter alia, been formed by the Fischer-Tropsch synthesis process is subsequently separated off in a carbon dioxide removal step (C), the $CO_2$ which has been separated off (d) is recirculated to the reverse shift reactor (R). In addition, small amounts of $CO_2$ (b) are discharged from the reaction process. The $CO_2$-depleted synthesis product is subjected to an olefin work-up (D) from which the olefins (O), preferably light olefins having $C_2$-$C_8$ chains, can then be obtained.

Figure 4:
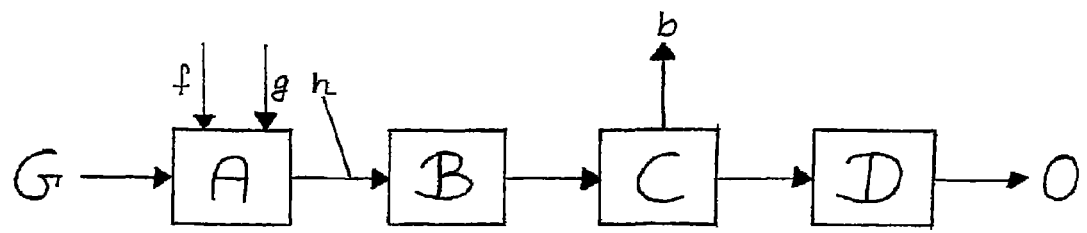
FIG. 4 depicts the preparation of olefins from natural gas via the Fischer-Tropsch reaction

FIG. 4 describes the preparation of olefins from natural gas via the Fischer-Tropsch reaction according to the prior art Natural gas (G), which preferably comprises methane, is firstly fed into the natural gas reformer (A). Oxygen (f) and/or water (g) are fed into this, as a result of which a synthesis gas mixture having a hydrogen to carbon monoxide ratio of about 2:1 (h) is obtained. This synthesis gas mixture is fed into the Fischer-Tropsch reactor (B), the resulting product is subjected to a carbon dioxide removal step (C) and the carbon dioxide liberated in the reaction is removed from the synthesis process. The crude product which remains is subjected to an olefin work-up (D) and the olefins (O) are then obtained therefrom.

EXAMPLES

Example 1

For the Fischer-Tropsch synthesis, a carbonyl iron powder catalyst having spherical primary particles was produced by a method analogous to WO 2009/013174. The reaction was carried out in a standard Fischer-Tropsch synthesis apparatus. The reaction temperature was 340° C. at a pressure of 25 bar. A synthesis gas mixture having a hydrogen to carbon monoxide ratio of 1:1 was set. The product composition was analyzed a total of 6 times at equal time intervals over a period of several hours. The average values are indicated below in [mol %]:
Carbon monoxide conversion: 98.6%
Proportion of $C_2$-$C_4$ fragments: 33%
of which olefins: 25.5%
of which saturated hydrocarbons: 7.5%
Proportion of methane gas: 13%.

Example 2

The trial was carried out by a method analogous to example 1, with the ratio of hydrogen to carbon monoxide in the synthesis gas being 0.9:1. The product composition was analyzed a total of 5 times at equal time intervals over a period of several hours. The average values are indicated below in [mol %]:
Carbon monoxide conversion: 97.0%
Proportion of $C_2$-$C_4$ fragments: 54%
of which olefins: 47%
of which saturated hydrocarbons: 7%
Proportion of methane gas: 10%.

Example 3

Comparative Example

The process was operated under reaction conditions analogous to example 1, with the ratio of hydrogen to carbon monoxide in the synthesis gas mixture being set to 2:1. The product composition was analyzed a total of 6 times at equal time intervals over a period of several hours. The average values are indicated below in [mol %]:
Carbon monoxide conversion: 98.1%
Proportion of $C_2$-$C_4$ fragments: 26.5%
of which olefins: 19%
of which saturated hydrocarbons: 7.5%
Proportion of methane gas: 16%.

As can be seen from examples 1 and 2 and the comparative example (example 3), both the total carbon yield (mol %) and the selectivity of $C_2$-$C_4$-olefins over aliphatic, saturated $C_2$-$C_4$-hydrocarbons can be controlled via the ratio of hydrogen to carbon monoxide in the synthesis gas mixture.F

The invention claimed is:
1. A process for preparing olefins, which comprises the following steps:
   a) preparation of a synthesis gas comprising carbon monoxide and hydrogen, wherein the synthesis gas is prepared from a mixture comprising hydrocarbons having a ratio of hydrogen to carbon of 0.5 to 4:1,
   b) introduction of carbon dioxide recirculated from step d) into the synthesis gas during or after the preparation of synthesis gas as per step a),
   c) conversion of the synthesis gas having a hydrogen to carbon monoxide ratio of <1.2:1 which is obtained in step b) into olefins in the presence of a Fischer-Tropsch catalyst,
   d) removal of the carbon dioxide comprised in the reaction product from step c), where the ratio of hydrogen to carbon monoxide in step c) is set via step b).
2. The process according to claim 1, wherein the Fischer-Tropsch catalyst in step c) is an iron- or cobalt-comprising heterogeneous catalyst.
3. The process according to claim 1, wherein the Fischer-Tropsch catalyst in step c) is a carbonyl iron powder catalyst having spherical primary particles.
4. The process according to claims 1, wherein $C_2$-$C_8$-olefins are prepared.
5. The process according to claim 1, wherein $C_2$-$C_4$-olefins are prepared.
6. The process according to claim 1, wherein the synthesis gas is prepared from methane and/or natural gas in step a).
7. The process according to claim 1, wherein the synthesis gas is prepared by a process selected from the group consisting of steam reforming, autothermal reforming, non-catalytic partial oxidation, catalytic partial oxidation, heat exchange reforming, compact reforming and dry reforming in step a).
8. The process according to claim 1, wherein the synthesis gas is prepared via a steam reforming or dry reforming process in step a).
9. The process according to claim 1, wherein the hydrogen to carbon monoxide ratio in step c) is from 1.2:1 to 1:1.2.
10. The process according to claims 1, wherein the hydrogen to carbon monoxide ratio in step c) is from 1.1:1 to 1:1.1.
11. The process according to claim 1, wherein the hydrogen to carbon monoxide ratio in step c) is 1:1.1.
12. The process according to claim 1, wherein the process temperature in step c) is from 100° C. to 500° C.
13. The process according to claim 1, wherein the pressure in step c) is in the range from 10 to 50 bar.

* * * * *